(12) United States Patent
Yamasaki

(10) Patent No.: US 6,399,106 B1
(45) Date of Patent: *Jun. 4, 2002

(54) METHOD FOR MAINTAINING FRESHNESS OF CUT FLOWER

(75) Inventor: Masahiko Yamasaki, Hino (JP)

(73) Assignee: Konica Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/094,033

(22) Filed: Jun. 9, 1998

(30) Foreign Application Priority Data

Jun. 13, 1997 (JP) ............................................. 9-156833
Jan. 27, 1998 (JP) ........................................... 10-029210
Jan. 28, 1998 (JP) ........................................... 10-015713

(51) Int. Cl.$^7$ .......................... A01N 59/16; A01N 3/02; A01N 31/00; A01N 33/02; A01N 55/02
(52) U.S. Cl. ....................... 424/618; 504/114; 504/115; 514/495; 514/673; 514/706; 514/707; 514/709
(58) Field of Search .......................... 424/618; 514/495, 514/549, 600, 601, 605, 606, 607, 75, 140, 141, 592, 507, 975, 706, 707, 709, 673; 504/114, 115

(56) References Cited

FOREIGN PATENT DOCUMENTS

| EP | 0281925 A | 9/1988 |
|---|---|---|
| EP | 0557946 A | 9/1993 |
| EP | 883990 A | 10/1998 |
| JP | XP002079202 | 10/1994 |
| JP | 6279201 | 10/1994 |

*Primary Examiner*—Jose' G. Dees
*Assistant Examiner*—Frank Choi
(74) *Attorney, Agent, or Firm*—Finnegan, Henderson Farabow, Garrett & Dunner, L.L.P.

(57) ABSTRACT

A method for maintaining the freshness of a cut flower is disclosed. The method comprises the step of causing a flowering plant to imbibe an aqueous solution of a composition for maintaining the freshness of flower which comprises a mixture or a reaction product of a silver compound and an organic compound having a functional group capable of forming a water-soluble complex with a silver ion through the sulfur atom thereof to a flowering plant.

10 Claims, No Drawings

METHOD FOR MAINTAINING FRESHNESS OF CUT FLOWER

FIELD OF THE INVENTION

The invention relates to a method for maintaining freshness of a cut flower by which the life of the cut flower can be considerably prolonged.

BACKGROUND OF THE INVENTION

Recently, cut flowers are widely used for ornamental use. As a result of that, it is demanded to maintain the freshness of the cut flower for a prolonged time. Various methods for maintaining the freshness of cut flower have been proposed. For example, a method of frequently changing water, a method of cutting the stem of flower in water and a method of burning the cut end of the flower, have been known. Furthermore, a method has been known in which the cut end of the flower is immersed in a solution containing a certain chemical. As the solution for the immersing, a solution of 8-hydroxyquinoline, a solution of sucrose, a solution of silver nitrate and a solution containing a silver thiosulfate complex are known.

However these methods are not always sufficient. In some cases, the methods are ineffective depending on the kind of the flower. For example, J. Am. Soc. Hort. Soci., 102, p. 76, 1977, reports that the moving speed of silver nitrate in the trachea of a plant is very slow and the effect of which is not clear. The silver-thiosulfate complex is ineffective to a flower having a low sensitivity to ethylene such as rose and chrysanthemum, even though the complex is effective to a flower having a high sensitivity for ethylene such as carnation, sweet pea and babies-breath. With respect to a cut flower of rose, a mixture and/or reaction product of a silver compound and an amino acid has been disclosed in Japanese Patent Publication Open for Public Inspection, hereinafter referred to JP O.P.I., No. 06-321701, and a mixture or a reaction product of a silver compound and a primary amine and/or a substance relating to nucleic acid has been disclosed in WO 93/08685. However, these compounds are insufficient in the effect thereof.

SUMMARY OF THE INVENTION

The object of the invention is to provide a method for maintaining the freshness of a cut flower by which the life of the flower can be considerably prolonged.

The objects of the invention are attained by a method for maintaining the freshness of a flower comprising the step of making imbibe an aqueous solution of a composition for maintaining the freshness of flower which comprises a mixture or a reaction product of a silver compound and an organic compound having a functional group capable of forming a water-soluble complex with a silver ion through the sulfur atom thereof to a flowering plant.

DETAILED DESCRIPTION OF THE INVENTION

As the functional group capable of forming a water-soluble complex with a silver ion through the sulfur atom thereof, the following are cited:

=C=S, =S=S, =S(=S)=, =P(=S)— and —S—.

Examples of the organic compound of the invention having a functional group capable of forming a water-soluble complex with a silver ion through the sulfur atom are those represented by the following Formula 1, 2, 3, 4 or 5.

Formula 1 wherein $R_1$ and $R_2$ are each a monovalent group which are each bonded with the carbon atom through a carbon atom, a nitrogen atom, an oxygen atom or a sulfur atom, provided that at least one of $R_1$ and $R_2$ is an organic group,

Formula 2 wherein $R_3$ and $R_4$ are each a monovalent group which are each bonded with the sulfur atom through a carbon atom, a nitrogen atom, an oxygen atom or a sulfur atom, provided that at least one of $R_3$ and $R_4$ is an organic group,

Formula 3 wherein $R_5$ and $R_6$ are each a monovalent group which are each bonded with the sulfur atom through a carbon atom, a nitrogen atom, an oxygen atom or a sulfur atom, provided that at least one of $R_1$ and $R_2$ is an organic group, and X is an oxygen atom or a sulfur atom.

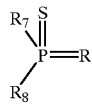

Formula 4 wherein $R_7$, $R_8$ and $R_9$ are each a monovalent group which are each bonded with the phosphor atom through a carbon atom, a nitrogen atom, an oxygen atom or a sulfur atom, provided that at least one of $R_7$, $R_8$ and $R_9$ is an organic group, $$R_{10}—S—R_{11}$$ Formula 5 wherein $R_{10}$ and $R_{11}$ are each a monovalent organic group.

In the foregoing Formulas 1 to 4, "through a carbon atom, a nitrogen atom, an oxygen atom or a sulfur atom" means the group represented by $R_1$, $R_2$, $R_3$, $R_4$, $R_5$, $R_6$, $R_7$, $R_8$, or $R_9$ each has a carbon atom, a nitrogen atom, an oxygen atom or a sulfur atom and the group is bonded through this atom with the carbon atom, sulfur atom or the phosphorous atom of Formula 1, 2, 3, or 4.

The =C=S group capable of forming a water-soluble complex with a silver ion through the sulfur atom includes, for example, a thiocarbonyl group, a thioacyl group, a thioamido group, a thioaldehyde group, a thioureido group, a thioureine group and an isothiocyanato group.

Examples of the organic compound having the =C=S group, a thioketone group, a thioaldehyde group, an O-carbothio acid and its ester, a thiourea derivative, a thioamide, a thioimide, and an isothiocyanate.

The foregoing thiourea derivative includes, for example, thiourea, N-methylthiourea, allyl-2-thiourea, 2-imidazolinethione, 1-allyl-3-β-hydroxyethyl-2-thiourea and 2-thiobarbituric acid.

As the compound having isothiocyanate, for example, ethyl isothiocyanate is cited.

As the organic compound having the =S=S group capable of forming a water-soluble complex with a silver ion through the sulfur atom, For example, a thiosulfinic acid derivative and its ester, and a thiosulfinamide are cited. In concrete, p-toluenethiosulfinamide is cited.

As the organic compound having =the S(=X)=S group capable of forming a water-soluble complex with a silver ion through the sulfur atom, for example, a thiosulfonic acid derivative and its ester are cited. In concrete, potassium p-toluenethiosulfonate and dimethylthiosulfuramide are cited.

As the organic compound having the =P(=S)— group capable of forming a water-soluble complex with a silver ion through the sulfur atom, for example, a thiophosphonic acid derivative and its ester and a thiophosphoric acid ester are cited. In concrete, for example, disodium methanethiophosphonate and dimethylthiophosphoramide are cited.

Examples of the compound represented by $R_{10}$—S—$R_{11}$, which is a compound having the —S— group capable of forming a water-soluble complex with a silver ion through the sulfur atom, include an organic sulfide, an S-ester of thiocarboxylic acid such as S-ester of carbothioacid, an ester of carbodithioacid, an S-ester of thiocarbonic acid such as S-ester of thiocarbonic acid, an S-ester of dithiocarbonic acid and an ester of trithiocarbonic acid.

As the foregoing organic sulfide compound, for example, a dithio compound such as 2,2'-thioglycolic acid, 2,2'-thiodiethanol, 3,3'-thiodipropionic acid, a polyalkylene thioglycol such as 3,6-dithia-1,8-octanediol are cited.

As example of ester of thiocarboxylic acid, S-methyl ester of 1-dihydroxyethyl-2carboxylic thio acid is cited.

As the silver compound in the invention, a monovalent silver compound is useful, and a silver salt is preferred. Example of the silver salt includes silver nitrate, silver carbonate, silver acetate, silver sulfate, silver chloride, and silver bromide.

The formation of water-soluble complex of the organic compound having a sulfur atom with a silver ion can be confirmed by measuring the silver electrode potential of the solution. When the complex is formed, the free silver ion concentration in the solution is lowered by the addition of the organic compound. The lowering of the silver ion concentration can be confirmed by lowering of the potential between the silver electrode and a reference electrode each immersed in the solution.

The composition of the invention for maintaining the freshness of cut flower can be prepared by mixing the silver compound and the organic compound having the functional group capable of forming a water-soluble complex or salt with a silver ion. The form of the composition of the invention for maintaining the freshness of cut flower is not specifically limited, and the composition may be in a form of solution, solid and powder. The form of an aqueous solution is most preferable.

The composition of the invention for maintaining the freshness of cut flower is preferably prepared by mixing an aqueous solution of the silver compound and an aqueous solution of the organic compound having the functional group capable of forming a water-soluble complex or salt with a silver ion.

The concentration of silver in the composition of the invention for maintaining the freshness of cut flower is from 0.001 millimoles/liter to 5 millimoles/liter, preferably from 0.005 millimoles/liter to 1 millimoles/liter, even though the concentration is not specifically limited. The molar ratio of silver to the organic compound having the functional group capable of forming a water soluble complex with a silver ion is preferably from 1/100 to 1,000, particularly preferably from 1 to 10.

It is preferred that the composition for maintaining the freshness of cut flower to be used in the invention is further contains a polycation compound or a surfactant.

The polyamine compound is a polymer having a constituting unit which has an amino group capable of forming a quaternary salt. A polyalkylimine is preferably usable as the polycation compound. For example, diethylenetriamine and triethylenetetramine, which are an oligomer of ethyleneimine, and a polyethyleneimine having a larger molecular weight are cited. The molecular weight of such the compound is preferably not more than 1000 even though the molecular weight is not specifically limited.

The concentration of the polycation in the freshness maintaining composition of the invention at the time of use is within the range of from 0.1 to 10, more preferably from 0.3 to 3, in the molar ratio of the cation unit and silver.

As the surfactant relating to the invention, any of a nonionic surfactant, a cationic surfactant and an anionic surfactant are usable, and the nonionic surfactant and the anionic surfactant are preferable. Concrete examples of the nonionic surfactant include a polyoxyethylene ether such as polyoxyethylene (10) octylphenyl ether which is available on the market under the trade name of TRITON X-100 manufactured by Kanto Kagaku Co., Ltd., polyoxyethylene cetyl ether and polyoxyethyele octyl ether, a polyoxyethylenesorbitan ether such as polyoxyethylenesorbitan monolaurate which is available on the market under the trade name of TWEEN-20 manufactured by Kanto Kagaku Co., Ltd., polyoxyethylenesorbitan monooleate, polyoxyethylenesorbitan monopalmitate, polyoxyethylenesorbitan monostearate and polyoxyethylenesorbitan trioleate, one having a cholic acid nucleus such a N,N-bis(3-D-gluconamido-propyl) cholamide, N,N-bis(3-D-gluconamidopropyl) dexycholamide and 3-(3-Cholamidopropyl)-(dimethylammonio)-2-hydroxyopropane-sulfonic acid, one having a sugar chain such as n-dodecyl-β-D-maltopyranoside, n-octyl-β-D-glucopyranoside, n-heptyl-β-D-thioglucopyranoside, n-octyl-β-D-thioglucopyranoside, sucrose monocaprate and sucrose monolaurate, and an alkane amide such as n-octyl-N-methylglucamide, n-nonanoyl-N-methylglucamide and n-decanoyl-N-methylglucamide. Examples of anionic surfactants include sodium dodecylsulfate (SDS), Sodium deoxycholic acid (DOC). TWEEN-20 and SDS are particularly preferable.

The concentration of the surfactant in the using of the freshness maintaining composition is within the range of from 0.00001% to 0.1%, preferably from 0.0001% to 0.05%, particularly preferably from 0.0005% to 0.005%, by weight in gram by volume in milliliter, hereinafter referred to W/V-%.

The composition of the invention is preferably has a pH of from 3 to 11. The composition of the invention for maintaining the freshness of cut flower may contains a buffering agent, an acid or an alkali to control the pH if it is necessary.

A sugar such as sucrose and glucose, an antibacterial agent such as 8-hydroxyquinoline, and a surfactant may be added as a additive according to necessity. A preservant such as a sulfite salt may also be added.

To imbibe the freshness maintaining composition according to the invention to the flower plant, the root of the flowering plant before cutting the flower or the cut end of a cut flower is immersed in an aqueous solution of the solution of the freshness maintaining composition. Thus the life of the cut flower can be prolonged.

Although there is no limitation on the time and the temperature of the immersion, it is preferred to immerse for 1 to 12 hours at a room temperature of from 20 to 25° C., and for 4 to 48 hours at a cold storage condition of from 2 to 10° C., when the composition is used for a pretreatment.

The freshness maintaining composition according to the invention may be used for a pretreatment, which has also a purpose of water raising, to be applied after picking up of the flower prior to the shipment. The freshness maintaining composition may also be used for a post-treatment of the flower to be applied in the distribution facilities such as a market and a flower shop or at a consumer.

Although there is no limitation on the flower to which the freshness maintaining composition to be applied, the composition is effective to, for example, rose, chrysanthemum, carnation, bouvardia, gerbera, babies-breath, and sweet pea. The composition is particularly effective to rose.

EXAMPLES

Example 1

1) Preparation of Freshness Maintaining Composition was dissolved in pure water to prepare an aqueous solution having a concentration of 0.1% by weight in gram by volume in milliliter, hereinafter referred to W/V-%. The solution of 1-allyl-2-thiourea and a 10 mM solution of silver nitrate were mixed in an appropriate amount of pure water to prepare a test solution 1-1 of the freshness maintaining composition. Furthermore, test solutions 1-2 through 1-4 were prepared in the same manner as in the solution 1-1 except that the kind the compound capable of forming a complex with a silver ion was changed as shown in Table 1. Moreover, a test solution 1-5 in which tris(hydroxymethyl) aminomethane was contained in place of the thiourea derivative, a test solution 1-6 in which sodium thiosulfate was contained in an amount of 6 times in moles of silver nitrate in place of the thiourea derivative, a test solution 1-7 containing silver nitrate only, and a test solution 1-8 composed of water only, were prepared for comparison.

2) Evaluation of Freshness Maintaining Effect

Flowers of rose (Rote Rose) were picked up and cut in a length of 40 cm. The cut flowers were grouped ten by ten. The cut ends of the flowers of each of the groups were respectively immersed in the test solution for 4 hours at 20° C. Then the test solution was changed to city water and stood at 20° C. The situation of the flowers was observed every day.

Results of the test are shown in Table 1. The vase life is an average of days until the flowers lose the appreciation value by the wilting, bent neck or opening center. The bent neck ratio is the percentage of the flower which have lost the appreciation value by the bent neck.

TABLE 1

| Test solution No. | Organic compound and its concentration (W/V-%) | Concentration of silver (mM) | Vase life (Days) | Bent neck ratio (%) |
|---|---|---|---|---|
| 1-1 (Inv.) | 1-allyl-2-thiourea (0.01) | 0.03 | 12.2 | 0 |
| 1-2 (Inv.) | 2-imidazolinethione (0.01) | 0.03 | 12.5 | 0 |

TABLE 1-continued

| Test solution No. | Organic compound and its concentration (W/V-%) | Concentration of silver (mM) | Vase life (Days) | Bent neck ratio (%) |
|---|---|---|---|---|
| 1-3 (Inv.) | 1-allyl-3-β-hydroxyethyl-2-thiourea (0.01) | 0.03 | 11.2 | 0 |
| 1-4 (Inv.) | 2-thiobarbituric acid (0.01) | 0.03 | 12.0 | 0 |
| 1-5 (Comp.) | Tris(hydroxymethyl)-aminomethane (0.01) | 0.03 | 6.4 | 100 |
| 1-6 (Comp.) | Sodium thiosulfate | 0.03 | 6.6 | 100 |
| 1-7 (Comp.) | None | 0.03 | 5.8 | 100 |
| 1-8 (Comp.) | None | 0 | 5.4 | 100 |

The flowers treated by the freshness maintaining composition were prevented from the bent neck and the life of them were prolonged.

Example 2

1) Preparation of the Freshness Maintaining Composition

Each of the following sulfide compounds was dissolved in pure water to prepare an aqueous solution having a concentration of 0.1 W/V-%. Each of the sulfide solutions and a 10 mM solution of silver nitrate were mixed in an appropriate amount of pure water to prepare a test solution of the freshness maintaining composition, respectively. Thus test solutions 2-1 through 2-4 were prepared. Moreover, a test solution 2-5 in which tris(hydroxymethyl) aminomethane was contained in place of the disulfide compound, a solution 2-6 containing silver nitrate only, and a test solution 2-7 composed of water only were prepared for comparison.

The test solutions were evaluated in the same manner as in Example 1. Results of the evaluation are shown in Table 2.

TABLE 2

| Test solution No. | Organic compound and its concentration (W/V-%) | Concentration of silver (mM) | Vase life (Days) | Bent neck ratio (%) |
|---|---|---|---|---|
| 2-1 (Inv.) | 2,2'-thioglycolic acid (0.01) | 0.03 | 12.2 | 0 |
| 2-2 (Inv.) | 2,2'-thiodiethanol (0.01) | 0.03 | 12.5 | 0 |
| 2-3 (Inv.) | 3,3'-thiopropionic acid (0.01) | 0.03 | 12.2 | 0 |
| 2-4 (Inv.) | 3,6-dithio-1,8-octanediol (0.01) | 0.03 | 12.0 | 0 |
| 2-5 (Comp.) | Tris(hydroxymethyl)-aminomethane (0.01) | 0.03 | 6.6 | 100 |
| 2-6 (Comp.) | None | 0.03 | 5.6 | 100 |
| 2-7 (Comp.) | None | 0 | 5.2 | 100 |

Example 3

1) Preparation of the Freshness Maintaining Composition

Each of the following various compounds was dissolved in pure water to prepare an aqueous solution having a concentration of 0.1 W/V-%. Each of these solutions and a 10 mM solution of silver nitrate were mixed in an appropriate amount of pure water to prepare a test solution of the freshness maintaining composition, respectively. Thus test solutions 3-1 to 3-4 were prepared. Moreover, a solution 3-5 containing silver nitrate only, and a test solution 3-6 composed of water only, were prepared for comparison.

The test solutions were evaluated in the same manner as in Example 1. Results of the evaluation are shown Table 3.

TABLE 3

| Test solution No. | Organic compound and its concentration (W/V-%) | Concentration of silver (mM) | Vase life (Days) | Bent neck ratio (%) |
|---|---|---|---|---|
| 3-1 (Inv.) | Sodium methanethiosulfate (0.01) | 0.03 | 10.2 | 20 |
| 3-2 (Inv.) | Dimethylthiophosphamide (0.01) | 0.03 | 11.0 | 10 |
| 3-3 (Inv.) | p-toluenethiosulfinamide (0.01) | 0.03 | 9.5 | 20 |
| 3-4 (Inv.) | Potassium p-toluene-sulfonate (0.0) | 0.03 | 10.2 | 10 |
| 3-5 (Comp.) | None | 0.03 | 5.8 | 100 |
| 3-6 (Comp.) | None | 0 | 5.4 | 100 |

Example 4

1) Preparation of the Freshness Maintaining Composition

Each of the following various compounds was dissolved in pure water to prepare an aqueous solution having a concentration of 0.1 W/V-%. Each of these solutions and a 10 mM solution of silver nitrate were mixed in an appropriate amount of pure water to prepare a test solution of the freshness maintaining composition, respectively. Thus test solutions 4-1 to 4-3 were prepared. Moreover, a test solution 4-4 containing silver nitrate only and a test solution 4-5 composed of water only were prepared for comparison.

2) Evaluation of Freshness Maintaining Effect

Flowers of carnation (Francisco) were picked up and cut in a length of 30 cm. The cut flowers were grouped five by five. The cut ends of the flowers of each of the groups were respectively immersed in the test solution for 4 hours at 20° C. Then the test solution was changed to city water and stood at 20° C. The situation of the flowers was observed on every day.

The evaluation was performed in the same manner as in Example 1.

TABLE 4

| Test solution No. | Organic compound and its concentration (W/V-%) | Concentration of silver (mM) | Vase life (Days) |
|---|---|---|---|
| 4-1 (Inv.) | 2-imidazolinethione (0.03) | 0.1 | 19.6 |
| 4-2 (Inv.) | 2,2-thiodiglycolic acid (0.03) | 0.1 | 16.4 |
| 4-3 (Inv.) | 3,6-dithio-1,8-octanediol (0.03) | 0.1 | 16.8 |
| 4-4 (Comp.) | None | 0.1 | 10.6 |
| 4-5 (Comp.) | None | 0 | 8.8 |

Example 5

1) Preparation of Freshness Maintaining Composition

In pure water, 2,2'-thioglycolic acid was dissolved to prepare an aqueous solution having a concentration of 0.1 W/V-%. This solution was mixed with a proper amount of a 10 mM silver nitrate solution and pure water and mixed with triethylenetetramine as a polycation. Then the pH of the solution was adjusted to 5.0 by acetic acid. Thus a test solution 5-1 of the freshness maintaining composition according to the invention was prepared. Furthermore, test solutions 5-2 through 5-12 were prepared in the same manner as in the solution 5-1 except that the kind and the concentration of the polycation were changed as shown in Table 5. The final concentration of 2,2'-thioglycolic acid and silver in each of the test solution of the freshness maintaining composition were 0.01 W/V-% and 0.03 mM, respectively. Besides, test solutions 5-14 through 5-22 containing no 2,2'-thioglycolic acid and/or silver, a test solution 5-13 containing no polycation, and a test solution 5-23 composed of pure water only, were prepared for comparison.

2) Evaluation of Freshness Maintaining Effect

Flowers of rose (Rote Rose) were picked up and cut in a length of 40 cm. The cut flowers were grouped ten by ten. The cut ends of the flowers of each of the groups were respectively immersed in the test solution prepared in the above-mentioned 1) for 4 hours at 20° C. Then the flowers take out from the test solution and wrapped by newspaper and stored for 24 hours at 20° C. After the storage, the flowers were immersed in city water and stood at 20° C. The situation of the flowers was observed day by day.

Results of the test are shown in Table 5. The vase life was evaluated in the same norm as in Example 1. The flowering ratio is the percentage of the flower which can be completely flowered without loosing the appreciation value thereof.

TABLE 5

| Test solution No. | 2,2'-thioglycolic acid (a) and silver nitrate (b) | Polycation | Concentration of polycation (W/V-%) | Vase life (days) | Flowering ratio (%) |
|---|---|---|---|---|---|
| 5-1 (Inv.) | (a) and (b) | Thiethylenetetramine | 0.00003 | 10.0 | 80 |
| 5-2 (Inv.) | (a) and (b) | Triethylenetetramine | 0.0001 | 10.8 | 90 |
| 5-3 | (a) and (b) | Triethylenetetramine | 0.0003 | 11.6 | 90 |

TABLE 5-continued

| Test solution No. | 2,2'-thio-glycolic acid (a) and silver nitrate (b) | Polycation | Concentration of polycation (W/V-%) | Vase life (days) | Flowering ratio (%) |
|---|---|---|---|---|---|
| 5-4 (Inv.) | (a) and (b) | Triethylenetetramine | 0.001 | 9.8 | 80 |
| 5-5 (Inv.) | (a) and (b) | Polyethyleneimine (mw: 1000) | 0.00003 | 10.2 | 80 |
| 5-6 (Inv.) | (a) and (b) | Polyethyleneimine (mw: 1000) | 0.0001 | 11.2 | 90 |
| 5-7 (Inv.) | (a) and (b) | Polyethyleneimine (mw: 1000) | 0.0003 | 12.2 | 100 |
| 5-8 (Inv.) | (a) and (b) | Polyethyleneimine (mw: 1000) | 0.001 | 10.8 | 90 |
| 5-9 (Inv.) | (a) and (b) | Polyethyleneimine (mw: 300) | 0.00003 | 10.2 | 80 |
| 5-10 (Inv.) | (a) and (b) | Polyethyleneimine (mw: 300) | 0.0001 | 12.4 | 100 |
| 5-11 (Inv.) | (a) and (b) | Polyethyleneimine (mw: 300) | 0.0003 | 12.6 | 100 |
| 5-12 (Inv.) | (a) and (b) | Polyethyleneimine (mw: 300) | 0.001 | 11.5 | 90 |
| 5-13 (Inv.) | (a) and (b) | None | — | 8.2 | 60 |
| 5-14 (Comp.) | None | Triethylenetetramine | 0.0001 | 3.8 | 10 |
| 5-15 (Comp.) | None | Polyethyleneimine (mw: 1000) | 0.0001 | 4.8 | 20 |
| 5-16 (Comp.) | None | Polyethyleneimine (mw: 300) | 0.0001 | 4.2 | 10 |
| 5-17 (Comp.) | Only (a) | Triethylenetetramine | 0.0001 | 3.6 | 10 |
| 5-18 (Comp.) | Only (a) | Polyethyleneimine (mw: 1000) | 0.0001 | 4.6 | 20 |
| 5-19 (Comp.) | Only (a) | Polyethyleneimine (mw: 300) | 0.0001 | 4.0 | 10 |
| 5-20 (Comp.) | Only (b) | Triethylenetetramine | 0.0001 | 4.6 | 20 |
| 5-21 (Comp.) | Only (b) | Polyethyleneimine (mw: 1000) | 0.0001 | 4.4 | 20 |
| 5-22 (Comp.) | Only (b) | Polyethyleneimine (mw: 300) | 0.0001 | 4.8 | 30 |
| 5-23 (Comp.) | None | None | — | 3.0 | 0 |

Example 6

1) Preparation of Freshness Maintaining Composition

In pure water, 3,6-dithia-1,8-octanediol was dissolved to prepare an aqueous solution having a concentration of 0.1 W/V-%. This solution was mixed with a proper amount of a 10 mM silver nitrate solution and pure water, and then mixed with polyoxyethylenesorbitan monolaurate and the polycation. Then the pH of the solution was adjusted to 5.0 by glycolic acid. Thus a test solution 6-1 of the freshness maintaining composition according to the invention was prepared. The final concentrations of 3,6-dithia-11,8-octanediol, silver and polyoxyethylenesorbitan monolaurate in the each of test solutions of the freshness maintaining composition were 0.018 W/V-%, 0.06 mM, and 0.001 W/V-%, respectively. Furthermore, test solutions 6-2 through 6-12 were prepared in the same manner as in the test solution 6-1. except that the kind and the concentration of the polycation were changed as shown in Table 6. Besides, test solutions 6-14 through 6-16 containing no 3,6-dithia-1,8-octanediol and silver compound, a test solution 6-13 containing no polycation, and a test solution 6-17 composed of pure water only, were prepared for comparison.

2) Evaluation of Freshness Maintaining Effect

The evaluation was performed in the same manner as Example 5. Results are shown in Table 6.

TABLE 6

| Test solution No. | 3,6-dithia-1,8-octanediol and silver | Polycation | Concentration of polycation (W/V-%) | Vase life (days) | Flowering ratio (%) |
|---|---|---|---|---|---|
| 6-1 (Inv.) | Presence | Triethylene-tetramine | 0.0001 | 11.8 | 90 |
| 6-2 (Inv.) | Presence | Triethylene-tetramine | 0.0003 | 11.0 | 90 |
| 6-3 (Inv.) | Presence | Triethylene-tetramine | 0.001 | 11.6 | 90 |
| 6-4 (Inv.) | Presence | Triethylene-tetramine | 0.003 | 9.8 | 70 |
| 6-5 (Inv.) | Presence | Polyethyleneimine (mw: 1000) | 0.0001 | 11.6 | 90 |
| 6-6 (Inv.) | Presence | Polyethyleneimine (mw: 1000) | 0.0003 | 12.6 | 100 |
| 6-7 (Inv.) | Presence | Polyethyleneimine (mw: 1000) | 0.001 | 11.0 | 90 |
| 6-8 (Inv.) | Presence | Polyethyleneimine (mw: 1000) | 0.003 | 10.8 | 80 |
| 6-9 (Inv.) | Presence | Polyethyleneimine (mw: 300) | 0.0001 | 11.2 | 90 |

TABLE 6-continued

| Test solution No. | 3,6-dithia-1,8-octane-diol and silver | Polycation | Concentration of polycation (W/V-%) | Vase life (days) | Flowering ratio (%) |
|---|---|---|---|---|---|
| 6-10 (Inv.) | Presence | Polyethyleneimine (mw: 300) | 0.0003 | 12.4 | 100 |
| 6-11 (Inv.) | Presence | Polyethyleneimine (mw: 300) | 0.001 | 12.6 | 100 |
| 6-12 (Inv.) | Presence | Polyethyleneimine (mw: 300) | 0.003 | 10.6 | 80 |
| 6-13 (Inv.) | Presence | none | — | 8.2 | 60 |
| 6-14 (Comp.) | None | Triethylenetetramine | 0.0003 | 4.2 | 10 |
| 6-15 (Comp.) | None | Polyethyleneimine (mw: 1000) | 0.0003 | 3.8 | 10 |
| 6-16 (Comp.) | None | Polyethyleneimine (mw: 300) | 0.0003 | 4.2 | 10 |
| 6-17 (Comp.) | None | None | — | 3.4 | 0 |

Example 7

1) Preparation of Freshness Maintaining Composition

A 0.5 W/V-% aqueous solution of the organic compound capable of forming a water-soluble complex with silver ion through the sulfur atom, a 10 mM aqueous solution of silver nitrate and polycation were mixed in pure water and pH of the mixture was adjusted to 5.0 by glycolic acid. Thus a test solution 7-1 of the freshness maintaining composition was prepared. Furthermore, test solutions 7-2 through 7-4 were prepared in the same manner as in the test solution 7-1 except that the combination of the compound capable of forming a silver complex and the polycation was changed as shown in Table 7. In these solutions, the final concentrations of the organic compound and silver were 0.06 W/V-% and 0.2 mM, respectively. A test solution containing no polycation and a test solution composed of pure water only were prepared for comparison.

2) Evaluation of Freshness Maintaining Effect

Flowers of carnation (Francisco) were picked up and cut in a length of 30 cm. The cut flowers were grouped five by five. The cut ends of the flowers of each of the groups were respectively immersed in the test solution for 4 hours at 20° C. Then the test solution was changed to city water and stood at 20° C. The situation of the flowers was observed day by day.

The evaluation was performed in the same manner as Example 5. Results of the test are shown in Table 7.

TABLE 7

| Test No. | Compound capable of forming a complex with silver | Kind and concentration of polycation (W/V-%) | Vase life (days) |
|---|---|---|---|
| 7-1 (Inv.) | 2,2'-thioglycolic acid | Triethylenetetramine 0.001 | 17.8 |
| 7-2 (Inv.) | 2,2'-thioglycolic acid | None | 15.4 |
| 7-3 (Inv.) | 3,6-dithia-1,8-octane-diol | Polyethyleneimine (mw: 300) 0.001 | 18.2 |
| 7-4 (Inv.) | 3,6-dithia-1,8-octane-diol | None | 15.6 |
| 7-2 (Comp.) | None | None | 8.0 |

Example 8

1) Preparation of Freshness Maintaining Composition

In pure water, 2,2'-thioglycolic acid was dissolved to prepare an aqueous solution having a concentration of 0.1 W/V-%. This solution was mixed with a proper amount of a 10 mM silver nitrate solution and pure water and mixed with a surfactant SDS. Thus a test solution 8-1 of the freshness maintaining composition according to the invention was prepared. Furthermore, test solutions 8-2 through 8-16 were prepared in the same manner as in the test solution 8-1 except that the kind and the concentration of the surfactant were changed as shown in Table 8. The final concentrations of 2,2'-thioglycolic acid and silver in the each of the test solutions of the freshness maintaining composition were 0.01 W/V-% and 0.03 mM, respectively. Besides, a test solution 8-7 containing no surfactant, test solutions 8-18 through 8-21 containing no 2,2'-thioglycolic acid and silver compound, and a test solution 8-22 composed of pure water only, were prepared for comparison.

2) Evaluation of Freshness Maintaining Effect

Flowers of rose (Rote Rose) were picked up and cut in a length of 40 cm. The cut flowers were grouped ten by ten. The cut ends of the flowers of each of the groups were respectively immersed in the test solution prepared in the above-mentioned 1) for 4 hours at 20° C. Then the flowers take out from the test solution and wrapped by newspaper and stored for 24 hours at 20° C. After the storage, the flowers were immersed in city water and stood at 20° C. The situation of the flowers was observed day by day.

The evaluation was performed in the same manner as Example 5. Results of the test are shown in Table 8.

TABLE 8

| Test solution No. | 2,2-thioglycolic acid and silver compound | Kind of surfactant | Concentration of surfactant (W/V-%) | Vase life (days) | Flowering ratio (%) |
|---|---|---|---|---|---|
| 8-1 (Inv.) | Presence | SDS | 0.0005 | 11.0 | 90 |
| 8-2 (Inv.) | Presence | SDS | 0.002 | 12.2 | 100 |
| 8-3 (Inv.) | Presence | SDS | 0.005 | 12.6 | 100 |
| 8-4 (Inv.) | Presence | SDS | 0.02 | 10.6 | 80 |
| 8-5 (Inv.) | Presence | TWEEN-20 | 0.0005 | 12.3 | 100 |
| 8-6 (Inv.) | Presence | TWEEN-20 | 0.002 | 11.9 | 100 |
| 8-7 (Inv.) | Presence | TWEEN-20 | 0.005 | 12.3 | 100 |
| 8-8 (Inv.) | Presence | TWEEN-20 | 0.02 | 9.8 | 80 |
| 8-9 (Inv.) | Presence | TRITON X-100 | 0.0005 | 9.2 | 80 |
| 8-10 (Inv.) | Presence | TRITON X-100 | 0.002 | 9.3 | 80 |
| 8-11 (Inv.) | Presence | TRITON X-100 | 0.005 | 8.6 | 70 |
| 8-12 (Inv.) | Presence | TRITON X-100 | 0.02 | 8.5 | 70 |
| 8-13 (Inv.) | Presence | DOC | 0.0005 | 8.9 | 70 |
| 8-14 (Inv.) | Presence | DOC | 0.002 | 9.5 | 80 |
| 8-15 (Inv.) | Presence | DOC | 0.005 | 9.0 | 70 |
| 8-16 (Inv.) | Presence | DOC | 0.02 | 8.6 | 60 |
| 8-17 (Inv.) | Presence | None | — | 8.2 | 60 |

TABLE 8-continued

| Test solution No. | 2,2-thio-glycolic acid and silver compound | Kind of surfactant | Concentration of surfactant (W/V-%) | Vase life (days) | Flowering ratio (%) |
|---|---|---|---|---|---|
| 8-18 (Comp.) | None | SDS | 0.002 | 3.6 | 10 |
| 8-19 (Comp.) | None | TWEEN-20 | 0.002 | 4.0 | 20 |
| 8-20 (Comp.) | None | TRITON X-100 | 0.002 | 3.4 | 10 |
| 8-21 (Comp.) | None | DOC | 0.002 | 3.5 | 10 |
| 8-22 (Comp.) | None | None | — | 3.0 | 0 |

SDS: Sodium dodecylsulfate
TWEEN-20: Polyoxyethylenesorbitan monolaurate.
TRITON X-100: Octylphenyl ether
DOC: Sodium deoxycholate Example 9

1) Preparation of Freshness Maintaining Composition

In pure water, 3,6-dithia-1,8-octanediol was dissolved to prepare an aqueous solution having a concentration of 0.1 W/V-%. This solution was mixed with a proper amount of a 10 mM silver nitrate solution and pure water, and then mixed with the surfactant SDS. Thus a test solution 9-1 of the freshness maintaining composition according to the invention was prepared. Furthermore, test solutions 9-2 through 9-16 were prepared in the same manner as in the test solution 9-1 except that the kind and the concentration of the surfactant were changed as shown in Table 9. The final concentrations of 3,6-dithia-1,8-octanediol, silver and polyoxyethylenesorbitan monolaurate in these test solutions were 0.018 W/V-% and 0.06 mM, respectively. Besides, a test solution 9-17 containing no surfactant, test solutions 9-18 through 9-21 containing no 3,6-dithia-1,8-octanediol and silver compound, and a test solution 9-22 composed of pure water only, were prepared for comparison.

2) Evaluation of Freshness Maintaining Effect

The evaluation was performed in the same manner as Example 5. Results are shown in Table 9.

TABLE 9

| Test solution No. | 3,6-dithia-1,8-octanediol and silver compound | Kind of surfactant | Concentration of surfactant (W/V-%) | Vase life (days) | Flowering ratio (%) |
|---|---|---|---|---|---|
| 9-1 (Inv.) | Presence | SDS | 0.0005 | 11.0 | 90 |
| 9-2 (Inv.) | Presence | SDS | 0.002 | 12.4 | 100 |
| 9-3 (Inv.) | Presence | SDS | 0.005 | 12.6 | 100 |
| 9-4 (Inv.) | Presence | SDS | 0.02 | 11.6 | 90 |
| 9-5 (Inv.) | Presence | TWEEN-20 | 0.0005 | 11.3 | 90 |
| 9-6 (Inv.) | Presence | TWEEN-20 | 0.002 | 12.0 | 100 |
| 9-7 (Inv.) | Presence | TWEEN-20 | 0.005 | 12.6 | 100 |
| 9-8 (Inv.) | Presence | TWEEN-20 | 0.02 | 10.9 | 90 |
| 9-9 (Inv.) | Presence | TRITON X-100 | 0.0005 | 9.6 | 80 |
| 9-10 (Inv.) | Presence | TRITON X-100 | 0.002 | 10.2 | 90 |
| 9-11 (Inv.) | Presence | TRITON X-100 | 0.005 | 8.8 | 70 |
| 9-12 (Inv.) | Presence | TRITON X-100 | 0.02 | 8.6 | 70 |
| 9-13 (Inv.) | Presence | DOC | 0.0005 | 8.9 | 70 |
| 9-14 (Inv.) | Presence | DOC | 0.002 | 9.7 | 80 |
| 9-15 (Inv.) | Presence | DOC | 0.005 | 9.2 | 70 |
| 9-16 (Inv.) | Presence | DOC | 0.02 | 8.8 | 60 |
| 9-17 (Inv.) | Presence | None | — | 8.6 | 60 |
| 9-18 (Comp.) | None | SDS | 0.002 | 3.5 | 10 |
| 9-19 (Comp.) | None | TWEEN-20 | 0.002 | 3.9 | 20 |
| 9-20 (Comp.) | None | TRITON X-100 | 0.002 | 3.4 | 10 |
| 9-21 (Comp.) | None | DOC | 0.002 | 3.6 | 10 |
| 9-22 (Comp.) | None | None | — | 3.1 | 0 |

Example 10

1) Preparation of Freshness Maintaining Composition

A 0.5 W/V-% aqueous solution of the organic compound capable of forming a water-soluble complex with silver ion through the sulfur atom, a 10 mM aqueous solution of silver nitrate, and the surfactant SDS were mixed in a proper amount of pure water. Thus a test solution 10-1 of the freshness maintaining composition was prepared. Furthermore, a test solutions 10-3 was prepared in the same manner as in the solution 10-1 except that the the compound capable of forming a silver complex and the surfactant were changed as shown in Table 10. In these solutions, the final concentrations of the organic compound and silver compound were 0.06 W/V-% and 0.2 mM, respectively. Besides, test solutions 10-2 and 2-4 containing no surfactant and a test solution 2-5 composed of pure water only were prepared for comparison.

2) Evaluation of Freshness Maintaining Effect

Flowers of carnation (Francisco) were picked up and cut in a length of 30 cm. The cut flowers were grouped five by five. The cut ends of the flowers of each of the groups were respectively immersed in the test solution for 4 hours at 20° C. Then the test solution was changed to city water and stood at 20° C. The situation of the flowers was observed day by day.

TABLE 10

| Test solution No. | Compound capable of forming a complex with silver | Kind and concentration of surfactant (W/V-%) | Vase life (days) |
|---|---|---|---|
| 10-1 (Inv.) | 2,2'-thioglycolic acid | SDS/0.001 | 18.0 |

TABLE 10-continued

| Test solution No. | Compound capable of forming a complex with silver | Kind and concentration of surfactant (W/V-%) | Vase life (days) |
|---|---|---|---|
| 10-2 (Inv.) | 2,2'-thioglycolic acid | None | 16.2 |
| 10-3 (Inv.) | 3,6-dithia-1,8-octane-diol | Tween-20/0.001 | 18.8 |
| 10-4 (Inv.) | 3,6-dithia-1,8-octane-diol | None | 16.6 |
| 10-5 (Comp.) | None | None | 8.4 |

What is claimed is:

1. A method for maintaining the freshness of a flower comprising causing a flowering plant to imbibe an aqueous solution of a composition for maintaining the freshness of flower which comprises a mixture or a reaction product of a silver compound and an organic compound having a functional group capable of forming a water-soluble complex with a silver ion through the sulfur atom thereof, wherein the organic compound is an organic sulfide represented by Formula 5, $$R_{10}-S-R_{11} \quad (5)$$

wherein $R_{10}$ and $R_{11}$ are each monovalent organic groups.

2. The method of claim 1, wherein the step of causing a flowering plant to imbibe the composition for maintaining the freshness of flower is carried out by immersing the cut end of the flowering plant in an aqueous solution of the composition for maintaining the freshness of flower.

3. The method of claim 1, wherein the step of causing a flowering plant to imbibe the composition for maintaining the freshness of flower is carried out by immersing the root of the flowering plant to an aqueous solution of the composition for maintaining the freshness of flower.

4. The method of claim 1, wherein the content of the silver compound in the aqueous solution of the composition for maintaining the freshness of flower is from 0.001 millimoles to 5 millimoles per liter, and the mole ratio of the silver compound to the organic compound having a functional group capable of forming a water-soluble complex with a silver ion through the sulfur atom thereof is from 1/100 to 1000.

5. The method of claim 1, wherein the composition for maintaining the freshness of flower further contains a polycation.

6. The method of claim 5, wherein the polycation is a polyalkyleneimine.

7. The method of claim 5, wherein the content of the polycation in aqueous solution of the composition for maintaining the freshness of flower is from 0.1 to 10 in the mole ratio of the cation unit of the polycation to silver.

8. The method of claim 1, wherein the composition for maintaining the freshness of flower further contains a surfactant.

9. The method of claim 8, wherein the surfactant is a nonionic surfactant or an anionic surfactant.

10. The method of claim 8, wherein the content of the surfactant in aqueous solution of the composition for maintaining the freshness of flower is from 0.0001% to 0.1% by weight per volume.

* * * * *